United States Patent
Orfao De Matos Correia E Vale et al.

(10) Patent No.: US 7,321,843 B2
(45) Date of Patent: Jan. 22, 2008

(54) METHOD FOR GENERATING NEW FLOW CYTOMETRY DATA FILES CONTAINING AN INFINITE NUMBER OF DIMENSIONS BASED ON DATA ESTIMATION

(75) Inventors: José Alberto Orfao De Matos Correia E Vale, Salamanca (ES); Carlos Eduardo Pedreira, Rio de Janeiro (BR); Elaine Sobral Da Costa, Rio de Janerio (BR)

(73) Assignee: Universidad de Salamanca, Salamanca (ES)

( * ) Notice: Subject to any disclaimer, the term of this patent is extended or adjusted under 35 U.S.C. 154(b) by 0 days.

(21) Appl. No.: 11/240,167

(22) Filed: Sep. 30, 2005

(65) Prior Publication Data

US 2007/0078626 A1    Apr. 5, 2007

(51) Int. Cl.
*G06F 15/00* (2006.01)
(52) U.S. Cl. .................................................. 702/182
(58) Field of Classification Search ............... 702/21, 702/27, 30, 32, 182, 190; 435/2, 7.24, 7.1, 435/40.5; 436/64; 707/1, 104.1
See application file for complete search history.

(56) References Cited

U.S. PATENT DOCUMENTS

| | | | |
|---|---|---|---|
| 5,047,321 A | 9/1991 | Loken et al. | |
| 5,137,809 A | 8/1992 | Loken et al. | |
| 5,538,855 A | 7/1996 | Orfao | |
| 6,287,791 B1 | 9/2001 | Terstappen et al. | |
| 7,043,500 B2 * | 5/2006 | Leary | 707/104.1 |
| 2003/0215892 A1 | 11/2003 | Orfao De Matos Correia E Valle et al. | |
| 2004/0059519 A1 * | 3/2004 | Chandler et al. | 702/19 |
| 2004/0224371 A1 | 11/2004 | Orfao De Matos Correia E Valle et al. | |

* cited by examiner

*Primary Examiner*—Bryan Bui
(74) *Attorney, Agent, or Firm*—Collard & Roe, P.C.

(57) ABSTRACT

A method that generates new flow cytometry data files with a potentially infinite number of dimensions is described. First two or more separate flow cytometry data files containing information about events measured in different aliquots from the same sample are fused. Then, the magnitude of the values and a corresponding uncertainty measure of the differing variables between one or more of the original data files which have been fused are estimated, for each individual event contained in the fused data file, for which that variable was not directly measured in the flow cytometer. The new data file containing both data actually measured in the flow cytometer for each event of the individual original data files fused and the estimated data for those parameters not measured in a group of events from one or more of the original data files are reconstructed multidimensionally.

40 Claims, 1 Drawing Sheet

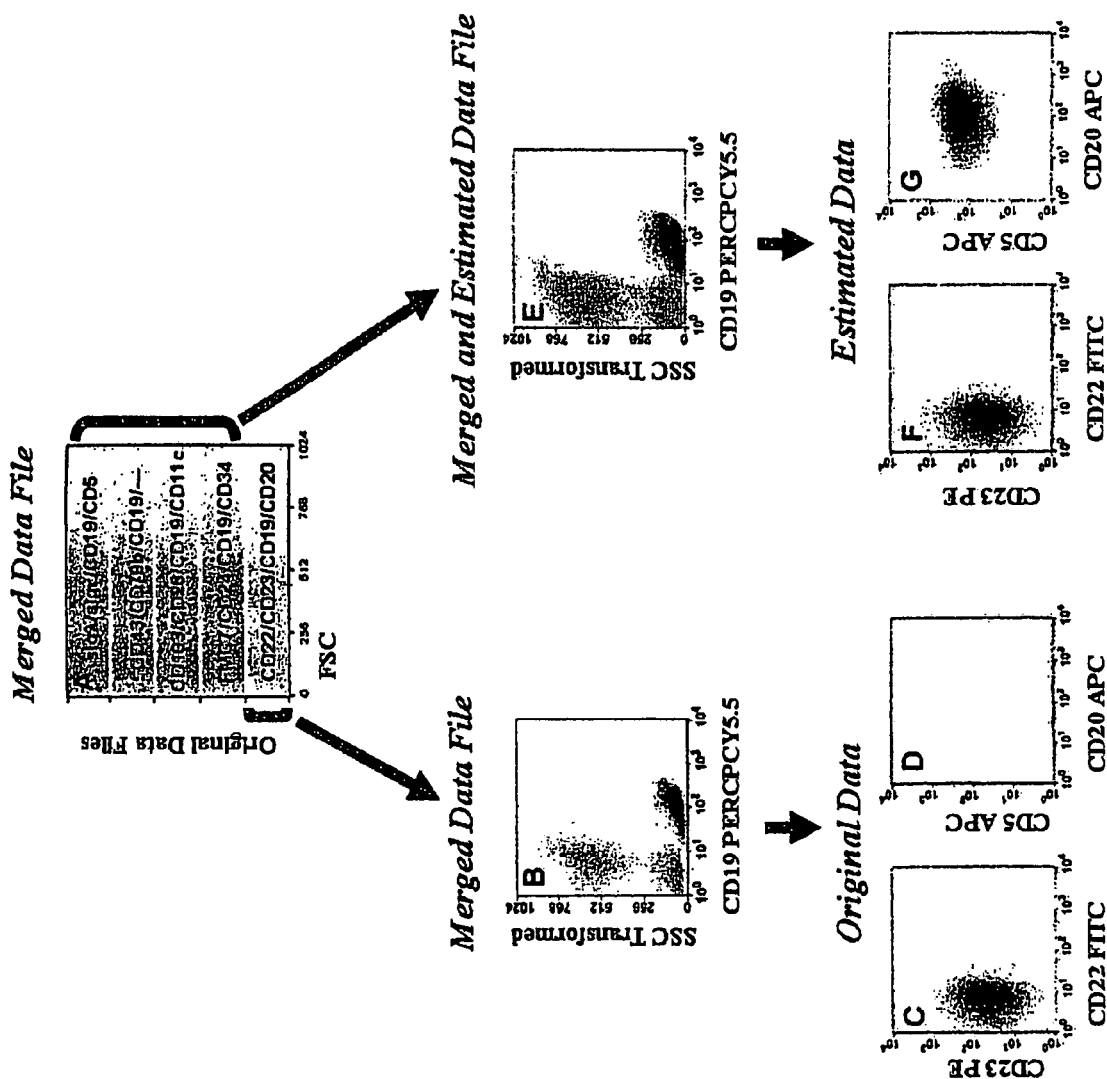

METHOD FOR GENERATING NEW FLOW CYTOMETRY DATA FILES CONTAINING AN INFINITE NUMBER OF DIMENSIONS BASED ON DATA ESTIMATION

"Generation of flow cytometry data files with a potentially infinite number of dimensions derived from the fusion of a group of separate flow cytometry data files and their multidimensional reconstruction with both actually measured and estimated flow cytometry data".

FIELD OF THE INVENTION

This invention relates to the field of flow cytometry and more particularly to the generation of new flow cytometry data files with a potentially infinite number of dimensions, each individual event included in these new data files having associated information which has been actually measured or estimated, for all individual parameters evaluated. These new flow cytometry data files are created by: 1) fusing a group of separate flow cytometry data files containing information about events measured in different aliquots from the same sample; these original data files contain, in common, data about one or more parameters at the same time they contain information about one or more different parameters; 2) estimating the magnitude of the values and of a corresponding uncertainty measure of the differing variables between one or more of the original data files which have been fused for each individual event contained in the fused data file for which that variable was not directly measured in the flow cytometer and; 3) reconstructing multidimensionally the new data file containing both the real data measured in the flow cytometer for each event of the individual original data files fused and the estimated data for those parameters not measured in a group of events from each of the original data files. This invention enables the generation of data files containing information for single cellular events from a sample about a higher number of parameters than those actually measured in each of the original data files fused; the overall number of parameters for which values are assigned to each individual cellular event included in the new data file is only limited by the total number of parameters measured in the whole group of fused data files. This allows a more powerful identification, enumeration and characterization of different populations of events contained in a sample.

BACKGROUND OF THE INVENTION

Loken and Terstappen have previously described in U.S. Pat. No. 5,047,321, the multiparameter analysis of cellular components in a body fluid comprised of blood and bone marrow. These authors were able to discriminate among various cellular components of blood and bone marrow, count the number of cells within each component and provide a differential analysis of each of them using a combination of two nucleic acid dyes—the LDS-751 (Exciton) DNA-dye, the thiazol orange (TO, Molecular Probes, Inc) RNA-dye—, a fluorescently labeled anti-CD45 monoclonal antibody and two light scatter parameters (forward and sideward light scatter). This approach allowed the identification and differention between nucleated red cells, erythrocytes, reticulocytes, platelets, lymphocytes, monocytes, neutrophil granulocytes, basophilic granulocytes, eosinophilic granulocytes and precursors of all nucleated cells. Despite this, they could not show that with this approach they were capable of specifically differentiate between normal and neoplastic cells coexisting in the same sample or of further characterize these cell subsets.

In U.S. Pat. No. 6,287,791, Terstappen and Chen described a further refinement of the U.S. Pat. No. 5,047,321, but they did not show any better characterization of the different leukocyte populations.

In U.S. Pat. No. 0,238,009,8.0, Orfao described a procedure for the multidimensional leukocyte differential analysis of blood, bone marrow and other body fluids, which specifically allowed further identification of dendritic cells and their subsets, in addition to nucleated red cells, lymphocytes, monocytes, neutrophil granulocytes, basophilic granulocytes, eosinophilic granulocytes and precursors of all nucleated cells.

In turn, in U.S. Pat. No. 5,538,855, Orfao described a procedure that allowed a more detailed analysis of the lymphoid compartments through the simultaneous identification of up to 12 different subsets of T, B and Nk-cells in blood and bone marrow among other types of biological samples. The author used a combined staining for the CD3, CD19, CD56 (and/or CD16), CD4 and CD8 antigens in a 3-color single staining. However, by using this approach he was not able to further characterize the identified cell subsets, at the same time, not all subsets of non-lymphoid cells present in a normal peripheral blood could be specifically identified (e.g.: subpopulations of dendritic cells).

In none of the referred procedures, the methods described allowed directly for a more detailed characterization of the cells identified. In such case, the use of a greater number of stainings associated with distinguishable fluorescence emissions and of flow cytometer instruments capable of measuring a higher number of different fluorescence emissions, are required. In the past two decades, the number of different fluorescence emission that can be simultaneously measured by a flow cytometer has notably increased moving from 3 to up to 17 colors. However, this number is still limited since frequently more than 20 markers are required for a detailed characterization of the cellular components present in different normal and pathological samples. As an example, assessment of the TCRVbeta repertoire of peripheral blood TCRalfa-beta+ T-cells, typically requires staining for more than 20 different markers directed against different members of the TCRVbeta families of proteins; similarly, routine diagnostic immunophenotypic analysis of leukemic samples is based on the evaluation of the staining patterns of bone marrow and/or blood cells for up to several tenths of different markers (typically between 20 and 40 antigens). Thus, even with the ability of simultaneously measuring 17 different fluorescence emissions, the most advanced flow cytometry instruments still have limited multicolor capabilities. As mentioned above, the maximum number of simultaneously measured fluorescence emissions for an individual event or for a group of events contained in a flow cytometry data file, depends on the availability of fluorochromes with compatible, distinguishable fluorescence emissions and on the maximum number of fluorescence emissions that can be detected in the flow cytometer. Because of such limitation, staining of a sample for a number of markers higher than the number of fluorescence emissions that the available flow cytometer instrument is capable of measuring is usually done in two or more separate aliquots measured one after each other. As an example of such strategy, in U.S. Pat. No. 5,137,809, Loken and Sha described a procedure for a multiparameter analysis of cellular components in bone marrow. The authors described the use, in a first step, of a combination of monoclonal antibodies each labeled with a different fluorochrome, to stain all leukocytes and of further combinations to stain selected populations of leukocytes, in a second step. However, such approaches do not allow to automatically link and directly compare the information on the amount of light scatter and fluorescence emissions measured for individual cells contained 1) in different aliquots from the same sample, 2) in different samples derived from identical or different tissues from the same individual or from different individuals, or; 3) in different sample aliquots that have been measured under different conditions.

All procedures described above allowed the identification of a variable number of different populations of normal leukocytes present in blood, bone marrow and other samples and they only allow the identification of selected subpopulations of cells depending on the specific combination of monoclonal antibodies and nucleic acid dyes used; nevertheless, they were not able to provide an approach for the specific and reproducible identification of neoplastic cells admixtured naturally or artificially with normal cells in a sample.

In U.S. provisional patent No. 10/791.994, Orfao, Pedreira and Sobral da Costa described a procedure for the multidimensional detection of aberrant phenotypes in neoplastic cells to be used to discriminate them from normal cells, for monitoring minimal numbers of neoplastic cells in blood, bone marrow spinal fluid and lymph node samples, using flow cytometry measurements. This procedure also allows an objective comparison between flow cytometric data acquired in different measurements which corresponded to: 1) different aliquots from the same sample, 2) different aliquots from distinct samples from the same subject and 3) different aliquots from distinct samples from different individuals, even in cases where they were measured under different conditions. With this procedure, large flow cytometry data files are generated by merging data from two or more different data files containing data from one or more samples. In these data files, information about an infinite number of parameters can be stored together; however, each event in the list mode data file is only associated to data derived from the parameters actually measured in the flow cytometer for that particular event and no link can be made for individual events between the parameters that have been measured and those that have not been measured for that particular event, even if those parameters were evaluated for other events contained in the fused data file.

DESCRIPTION OF THE INVENTION

The present invention relates to a method that generates new flow cytometry data files with a potentially infinite number of dimensions, the events contained in these data files having associated information for each of the whole set of parameters evaluated, such information corresponding to data which has been either directly measured in the flow cytometer, or estimated afterwards. The invention comprises the steps of: 1) fusing two or more separate flow cytometry data files containing information about events measured in different aliquots from the same sample; these original data files contain, in common, data about one or more parameters at the same time they contain information about one or more different parameters, 2) estimating the magnitude of the values and of a corresponding uncertainty measure of the differing variables between one or more of the original data files which have been fused, for each individual event contained in the fused data file, for which that variable was not directly measured in the flow cytometer and; 3) reconstructing multidimensionally the new data file containing both the real data measured in the flow cytometer for each event of the individual original data files fused and the estimated data for those parameters not measured in a group of events from one or more of the original data files. This invention enables the generation of data files containing information for single cellular events from a sample about a higher number of parameters than those actually measured in the flow cytometer for the individual events contained in each of the original data files that have been fused; the overall number of parameters for which values are assigned to each individual cellular event included in the new data file can be as large as the total number of parameters measured in the whole group of fused data files. This allows a more powerful identification, enumeration and characterization of different populations of events contained in a sample.

According to this invention, prior to fusing the original flow cytometry data files two or more aliquots of a sample are separately stained with a panel of monoclonal antibodies. The sample may contain normal cells, neoplastic cells or a mixture of both normal and neoplastic cells. The sample may comprise peripheral blood, bone marrow, lymph node, spleen, ascitic fluid, spinal fluid, synovial fluid, pleural effusions and single cell suspensions prepared from a solid tissue. The panel of reagents used to stain the sample is formed by two or more combinations of monoclonal antibodies directly conjugated to fluorochromes. These combinations of fluorochrome-conjugated monoclonal antibodies consist of a combination of monoclonal antibody reagents, which are identical in all combinations and monoclonal antibody reagents which are only used in either one or part of all monoclonal antibody reagent combinations. Each combination of monoclonal antibody reagents may contain, in addition to the monoclonal antibodies, other probes to stain the sample. Said additional probes consist of fluorochromes specific for nucleic acid dyes, mitochondria, and other cell components (e.g.: zymogen granules, chromosomes, ions, proteins, lipids, carbohydrates) or cell functions (e.g. phagocytosis, secretion of proteins, activation, proliferation, differentiation). Each monoclonal antibody in each combination is conjugated to a different fluorochrome and each combination of monoclonal antibodies has, in common, one or more fluorochrome-conjugated monoclonal antibody reagents. The number of fluorescence emissions in each combination of multiple monoclonal antibodies comprises two or more different fluorochromes, each linked to a different monoclonal antibody, whose fluorescence emission is distinguishable from that of the other fluorochrome-conjugated monoclonal antibody reagents in that combination. The fluorochromes that can be used in this invention include fluorescein isothiocyanate (FITC), phycoerythrin (PE), peridin chlorophyll protein (PerCP), allophycocyanin, alexa fluor 488, alexa 647, alexa fluor 610, alexa 710, alexa fluor 405, cyanin 5 (Cy5), cyanin 5.5 (Cy5.5), Texas red (TR), pacific blue (PB), cascade yellow, cascade blue and conjugates there of coupled with PE, to APC or to PerCP (e.g. PE/Cy5, PE/Cy5.5, PE/Cy7, PE/TR, PerCP/Cy5.5, APC/Cy7), quantum dots or any additional compatible fluorochrome or fluorochrome tandem.

The exact sample preparation procedures used to stain the cells prior to measuring them in a flow cytometer have been previously described in detail and extensively used, and they can be easily implemented by an expert in the field.

After the sample is prepared and stained, the fluorescence emissions associated to large numbers of cells from the sample aliquots stained with each of the combinations of monoclonal antibodies is measured in a flow cytometer according to conventional procedures and, two or more independent list mode data files are stored; each of the stored data files contains information on the specific light scatter and fluorescence emission characteristics of the individual cells analyzed in each sample aliquot measured. For each sample aliquot either an identical or a different number of events may be measured in the flow cytometry. Alternatively, the information about two or more different sample aliquots can be stored in a single data file, directly after measured in the flow cytometry.

According to this invention, all those parameters common to each pair of sample aliquots are also common to all other sample aliquots measured whose information will be contained in the fused data file; alternatively, only part of all those parameters common to each pair of sample aliquots are also common to all other sample aliquots measured, whose information will be contained in the fused data file.

From the structural point of view, each of the stored data files consists of a matrix of data in which the information for each different cellular event measured is aligned in a single line, events which have been consecutively measured being placed in consecutive lines in the data matrix; for each event, information on its light scatter—forward (FSC) and sideward light scatter (SSC)—and its fluorescence emission-associated parameters is placed in a different column of the data matrix.

In order to fuse two or more list mode data files, the data from the files to be fused is pasted in a database in a known sequence. In the fused data file, each different parameter measured in the whole set of data files, related to the light scatter characteristics (FSC and SSC) and the fluorescence emissions of a cell is placed in a different column, whereas the data on each cellular event measured is placed in a different line. Events which come from the same initial data file are placed sequentially one after each other, ordered in a sequence which is directly or inversely related to the sequence they were measured in the flow cytometer. Alternatively, the original data files and the events contained in each of said data files are pasted in a sequence which is not related to the sequence that they were measured in the flow cytometer. Since only a part of all parameters were measured for events corresponding to each of the sample aliquots, in the fused data file, for each line (cellular event), there will be filled and unfilled columns which correspond to those parameters directly measured and to those parameters not evaluated in the flow cytometer for that particular event, respectively. The database columns may be ordered in a sequence, which is directly or inversely related to the order each parameter or group of parameters were measured. Alternatively columns in the fused database matrix may follow a different order. The empty database columns for each cellular event (line) will be then filled using similarity-based statistical estimation approaches to calculate values and a corresponding uncertainty measure for those parameters not measured for a group of events in the fused data file.

In order to fill all the empty database columns for each individual event, all the common fluorescence emissions measured plus the measures of light scatter are considered as 'common parameters' to all original data files and they may be variable in type and number (k=total number of 'common parameters' measured). In turn, the measures of all other fluorescence emissions recorded in the flow cytometer only for the events contained in part of all the original data files fused are considered as 'non-common parameters'. All data included in a fused data file corresponding to both the 'common parameters' and the 'non-common parameters' is measured in a variable number of sample aliquots (n=number of sample aliquots measured). Accordingly, $c_{ih}$ represents the $h^{th}$ non-common parameter of the $i^{th}$ sample aliquot, where i=1, ..., n and h=1, ... k. Similarly, $nc_{ih}$ represents the $h^{th}$ non-common parameter of the $i^{th}$ sample aliquot, where i=1, ..., n and h=1, ... m. If the number of events in each initial data file corresponding to a single sample aliquot is denoted as j, $c_{ih}$ and $nc_{ih}$ may be represented as vectors in $\Re^j$ for each i=1, ..., n, and h=1, ... k and for each i=1, ..., n, and h=1 respectively. Furthermore, if $c_{ih}(g)$, and $nc_{ih}(g)$ (where g represents the events measured in a sample aliquot) are considered as the $g^{th}$ components of vectors $c_{ih}$ and $nc_{ih}$, respectively, for a given event 's' (for each sample aliquot i=1, ..., n) $c_i(s) \equiv (c_{i1}(s), c_{i2}(s), ..., c_{ik}(s)) \in \Re^k$ and for a given event 'p' (for each tube i=1, ..., n) $nc_i(p) \equiv (nc_{i1}(p), nc_{i2}(p), ..., nc_{im}(p)) \in \Re^m$.

Based on the notations defined above, if two of the fused data files corresponding to two $-n_\alpha$ and $n_\beta$-sample aliquots, where $n_\alpha \neq n_\beta$ and $n_\alpha, n_\beta = 1$ a) Consider an event s, or a set of events $\Omega$. Take the value of $c_\alpha(s)$ (in sample aliquot $\alpha$). Alternatively, calculate any function $F_C(\Omega) \in \Re^k$ (e.g. $F_C(\Omega)$=mean $(c_\alpha(\xi))$ for $\xi \supset \Omega$). Note that one may have $\Omega$=s, and $F_C(\Omega) \equiv c_\alpha(\Omega) = c_\alpha(s)$, and so the later is in fact a generalization of the first.

b) Search in $n_\beta$ for those events "q" with any measurable similarity (e.g. the minimum distance, in which case one would use the nearest neighbors principle), to $c_\alpha(s)$ Alternatively, the same procedure with $F_C(\Omega)$ (instead of $c_\alpha(s)$). Let us assume that these "q" events are labeled as L ($L \in \Re^q$ is a set of labels). Then, build up a set $NC_\beta(L)$.

c) Evaluate the $nc_\beta(L)$ distribution and treat the situation in accordance with $nc_\beta(L)$ dispersion.

At the end of this process and after running the routine for all events corresponding to the $n_\alpha$ sample aliquot, all empty columns for the 'j' events corresponding to the $n_\alpha$ sample aliquot will be filled. In turn, after running the routine for all events and all pairs of sample aliquots, one will have built up a matrix with (n×j) lines and k+m columns that contain the information of k+m parameters for all (n×j) events.

According to what is described above, calculation of values and a corresponding uncertainty measure for those parameters not measured for a group of events in the fused data file, is performed for each individual event 's'; alternatively, calculation of values and a corresponding uncertainty measure for those parameters not measured for a group of events in the fused data file, is performed for a group '$\Omega$' of two or more events.

Furthermore, one or more of the measured parameters in one or more sample aliquots may also be estimated. Such estimation can be used as an internal quality control of the estimation procedure.

According to this invention, to calculate values and a corresponding uncertainty measure for those parameters not measured for a group of events in the fused data file, all parameters common to two or more sample aliquots or only part of them are used. In addition, in this invention, all events in the fused data file or only part of them, are used to calculate values and a corresponding uncertainty measure for those parameters not directly measured in the flow cytometry for a group of events of the fused data file.

The data contained in this new filled matrix may be analyzed using any conventional software program developed for the specific analysis of flow cytometry data files.

BRIEF DESCRIPTION OF THE DRAWING

The sole FIG. illustrates an example of the fusion and estimation processes performed on a set of five original flow cytometry data files corresponding to five aliquots of a peripheral blood sample from a patient diagnosed with a B-cell chronic lymphoproliferative disorder stained with five different combinations of fluorochrome conjugated monoclonal antibodies.

DETAILED EDSCRIPTION OF PREFERRED EMBODIMENTS

The sole FIG. illustrates an example of the fusion and estimation processes performed on a set of five original flow cytometry data files corresponding to five aliquots of a peripheral blood sample from a patient diagnosed with a B-cell chronic lymphoproliferative disorder stained with five different combinations of fluorochrome (fluorescein isothiocyanate -FITC-, phycoerythrin -PE-, peridinin choloryphyll protein/cyanin 5.5 -PerCP/Cy5.5- and allophycocyanin -APC-) conjugated monoclonal antibodies. Events from each of the five different data files were evaluated for three common parameters (forward -FSC- and sideward -SSC- light scatter and CD19) and 3 different cell surface antigens (data file 1: CD22, CD23, CD20; data file 2:). The data corresponding to the merged data files is shown in panel A; in this panel the X-axis represents staining for CD19 obtained for individual events in the different merged data files and in the Y-axis, events from the different merged data files are separately displayed. Data about those CD19+/SSC$^{lo}$ events (black dots) stained with the CD22/CD23/CD19/CD20 combination is depicted in panels B to D; in these panels it is shown how the CD19+/SSC$^{lo}$ events contained in this data file were selected (panel B) and illustrated that while CD22 and CD23 were originally measured simultaneously in this group of events (panel C), that was not the case for CD20 and CD5 (panel D). In the following dot plots (panels E to G), the same strategy was used for the selection of CD 19+/SSC$^{lo}$ events stained with combinations of monoclonal antibodies other than CD22/CD23/CD19/CD20 after performing data estimation for those parameters not directly measured for individual events contained in the fused data file; as shown in panels F and G, the pattern of expression of CD22 and CD23 observed for the estimated data is identical to that of the actually measured, original data (panel C). In addition, 2-dimensional dot-plot representations, corresponding to combinations of antibodies conjugated with the same fluorochrome but not obtained by direct staining of cells, were generated (e.g. pane G). In this example five different data files containing information about more than 15 parameters were merged; however, a higher number of data files could had been merged and data for the individual events contained in them estimated, generating a flow cytometry data file containing information about an infinite number of parameters for each individual event contained in it.

The invention will be illustrated by one example which do not limit its areas of application as follows:

EXAMPLE 1

1.—Sample:

Five mL of peripheral blood (PB) was obtained by venipuncture from one healthy volunteer and placed in a VACUTAINER™ (Becton Dickinson, New Jersey, N.J.) tube containing EDTA as anticoagulant.

2.—Sample Preparation:

After gentle mixing the sample, 200 uL of the PB sample containing $10^6$ nucleated cells was placed in five different replicate tubes. Then, to each tube, one of the following five 6-color combinations of monoclonal antibodies was added, each monoclonal antibody conjugated with a different fluorochrome (FITC/PE/PE-TR/PerCP-Cy5.5/APC/APC-Cy7) being added at saturating amounts in a volume of 5 uL:1) CD22/CD23/CD19/CD45/CD5/CD20, 2)CD43/CD79b/CD19/CD45/CD5/CD20, 3)CD9/CD27/CD19/CD45/CD5/CD20, 4)CD11c/CD10/CD19/CD45/CD5/CD20 and, 5)CD103/CD25/CD19/CD45/CD5/CD20. After gentle mixing, the sample aliquots were incubated for 15 minutes at room temperature in the darkness. After this incubation, 2 mL of FACSlysing solution (Becton Dickinson Biosciences, San José, Calif.), diluted 1/10 (vol/vol) in distilled water, was added. After gentle mixing, the stained and lysed sample aliquots were incubated for another 10 minutes at room temperature in the dark. Then, cells were centrifuged (5 minutes at 540 g), washed in 2 mL of phosphate buffered saline (PBS; pH=7.6) and resuspended in 500 uL of PBS/tube.

3.—Data Acquisition:

After gently mixing each stained sample aliquot, the light scatter and the fluorescence emissions of the stained cells were measured in a FACSARIA flow cytometer (Becton/Dickinson Biosciences—BDB—, San José, Calif.) equipped with two laser lights emitting at 488 and 635 nm, using the FACSDIVA (BDB) software programme. For each sample aliquot analyzed, a single data file was collected which contained information on the forward (FSC) and sideward light scatter (SSC), and the fluorescence emissions of FITC, PE, PE-TR, PE-Cy5.5, APC and APC-Cy7 for up to $5 \times 10^5$ cells/sample aliquot. In addition, information corresponding to the sequence of acquisition (time of acquisition) of each event was also recorded. Data acquisition was performed for the different tubes in the sequence defined in the above section about "sample preparation", using a FSC threshold set at 200.

4.—Data Manipulation and Data Analysis:

Data contained in each of the five data files generated was then exported into an excel database (Microsoft, Madrid, Spain) using the FCS 1a.a assistant software program (University of Stanford, Stanford, Calif.). Once place in the excel database, all five individual databases, each corresponding to a different sample aliquot, were fused into a single database where the first event measured from the second sample aliquot was placed in a line immediately after that corresponding to the last event measured for the first sample aliquot, the first event measured from the third sample aliquot was placed in a line immediately after that corresponding to the last event measured for the second sample aliquot, the first event measured from the fourth sample aliquot was placed in a line immediately after that corresponding to the last event measured for the third sample aliquot and the first event measured from the fifth sample aliquot was placed in a line immediately after that corresponding to the last event measured for the fourth sample aliquot. In addition, the following columns were created: column 1, FSC; column 2, SSC; column 3, CD22; column 4, CD23; column 5, CD19; column 6, CD45; column 7, CD5; column 8, CD20; column 9, CD43; column 10, CD79b; column 11, CD9; column 12, CD27; column 13, CD11c; column 14, CD10; column 15, CD103 and; column 16: CD25. Data corresponding to the sample aliquot stained with the CD22/CD23/CD19/CD45/CD5/CD20 multicolor combination of monoclonal antibody reagents was recorded in columns 1 to 8, both included, from line 1 to line 500,000; data measured for the second sample aliquot (CD43/CD79b/CD19/CD45/CD5/CD20 multicolor staining) was stored in columns 1, 2 and 5 to 10, from line 500,001 to line 1,000,000; for the third sample aliquot (CD9/CD27/CD19/CD45/CD5/CD20 staining) information was stored in columns 1, 2, 5 to 8, 11 and 12, from line 1,000,001 to line 1,500,000; data measured for the fourth sample aliquot (CD11c/CD10/CD19/CD45/CD5/CD20 staining) was stored in columns 1, 2, 5 to 8, 13 and 14, from line 1,500,001 to line 2,000,000; for the fifth sample aliquot (CD103/CD25/CD19/CD45/CD5/CD20 multicolor staining), information was recorded in columns 1, 2, 5 to 8, 15 and 16, from lines 2,000,001 to 2,500,000. The database cells remaining empty were filled afterwards with estimated data values, calculated as described below.

The common antibody-associated fluorescence emissions measured (CD19-PE-TR/CD45-PE-Cy5.5/CD5-APC/CD20-APC-Cy7) plus the measures of both forward (FSC) and sideward light scatter (SSC) were considered as the 'common parameters' "k" to all original data files (k=6, since the overall number of 'common parameters' was of 6). The fluorescence emission measures of all other monoclonal antibodies (CD22-FITC/CD23-PE/CD43-FITC/CD79b-PE/CD9-FITC/CD27-PE/CD11c-FITC/CD10-PE/CD103-FITC/CD25-PE) were considered as the 'non-common parameters' "m" (m=10, since the overall number of 'non-common parameters' was of 10). These common and non-common parameters were measured in the five sample aliquots "n" (n=5, corresponding to the five sample aliquots stained, prepared and measured in the flow cytometer). Accordingly, each of the original five data files stored corresponding to each of the five sample aliquots measured, contained six common parameters and two different parameters where $c_{ih}$ represents the $h^{th}$ (h=1, . . . 6) common parameter of the $i^{th}$ tube (i=1, 2, . . . 5) and $nc_{ih}$ represents the $h^{th}$ (h=1, . . . 10) non-common parameter of the $i^{th}$ tube (i=1, 2, . . . 5). The total number of events measured for each sample aliquot ("j") was of 500,000 events (j=500,000); therefore $c_{ih}$ and $nc_{ih}$ were represented as vectors in $\Re^{500000}$ for each i=1, . . . , 5 and h=1, . . . 6 and for each i=1, . . . , 5 and h=1, . . . 10, respectively. Furthermore, upon considering $c_{ih}(g)$, and $nc_{ih}(g)$ (for g=1, 2, . . . , 500,000) to be the $g^{th}$ components of vectors $c_{ih}$ and $nc_{ih}$, respectively, for a given event 's' and a given event 'p' (for each sample aliquot i=1, . . . , 5) we considered $c_i(s) \equiv (c_{i1}(s), c_{i2}(s), \ldots, c_{i6}(s)) \in \Re^6$ and $nc_i(p) \equiv (nc_{i1}(p), nc_{i2}(p), \ldots$ respectively. Considering the previously defined notation, a routine was run for sample aliquots $n_1$ and $n_2$, for each of the j events of $n_1$, as follows:

For a given event 's', the value of $c_1(s)$ in sample aliquot $n_1$ was calculated. Then the q nearest neighbors to $c_1(s)$ was searched in $n_2$. Afterward, a set of $nc_2(L)$ data points was built, assuming that these q points are labeled as L ($L \in \Re^q$ is a set of labels). If the built $nc_2(L)$ was compact and formed by a single cloud of data points), then we estimated $nc_{1\_EST}$=median($nc_2(L_{SUB})$), where $L_{SUB}$ is any subset of L. In turn, if $nc_2(L)$ was not compact and there were two or more clouds of data points), we calculated the probability of occurrence of each cloud, made a draw taking into account the probability of occurrence of each of the clouds, chose one of these clouds and estimated $nc_{1\_EST}$=median($nc_2(L_{SUB})$), where $L_{SUB}$ is any subset of L, just for the points in this cloud.

At the end of this process and after running the routine for all events corresponding to the $n_1$ sample aliquot, all empty columns for the 'j' events corresponding to the $n_1$ sample aliquot were filled. In turn, after running the routine for all events and all pairs of sample aliquots a matrix with 2,500,000 (500,000×5) lines and 16 (6+10) columns that contained the information of 16 parameters for all 2,500,000 events, was built. The data contained in this new filled matrix was then analyzed using a conventional flow cytometry software program (FACSDIVA software).

The invention claimed is:

1. A process for generating new flow cytometry data files with a potentially infinite number of dimensions, the data files containing events having associated information for each of a whole set of parameters evaluated, said information comprising measured data directly measured in a flow cytometer and data estimated after obtaining the measured data, comprising the steps of:
 a) fusing two or more separate original flow cytometry data files containing information about events measured in different aliquots of a same sample, the original data files containing in common data about one or more parameters and information about one or more different parameters;
 b) estimating a magnitude of the parameters and of a corresponding uncertainty measure for those parameters differing between one or more of the original data files, for each individual event contained in the fused data file, for which those variables were not directly measured in the flow cytometer and;
 c) reconstructing multidimensionally a new data file containing both the measured data measured in the flow cytometer for each event of the individual original data files and the estimated data for those parameters not measured in a group of events from one or more of the original data files.

2. The process according to claim 1, wherein prior to fusing the original flow cytometry data files, two or more aliquots of a sample are separately stained with a panel of monoclonal antibodies.

3. The process according to claim 1, wherein the sample contains normal cells, neoplastic cells or a mixture of both normal and neoplastic cells.

4. The process according to claim 2, wherein both the original data files and the fused data file comprise matrices of data in which each different parameter measured related to light scatter characteristics and fluorescence emissions of a cell is placed in a different column and the data on each event measured is placed in a different line.

5. The process according to claim 1, wherein the sample comprises peripheral blood.

6. The process according to claim 1, wherein the sample comprises bone marrow.

7. The process according to claim 1, wherein the sample comprises spinal fluid.

8. The process according to claim 1, wherein the sample comprises lymph node.

9. The process according to claim 1, wherein the sample comprises ascitic fluid.

10. The process according to claim 1, wherein the sample comprises pleural effusion.

11. The process according to claim 1, wherein the sample comprises synovial fluid.

12. The process according to claim 1, wherein the sample comprises a single cell suspension prepared from a solid tissue.

13. The process according to claim 1, wherein the panel of reagents is formed by two or more combinations of monoclonal antibodies directly conjugated to fluorochromes.

14. The process according to claim 13, wherein the combinations of fluorochrome-conjugated monoclonal antibodies used to stain distinct sample aliquots comprise monoclonal antibody reagents which are identical in all combinations and monoclonal antibody reagents which are only used in either one or part of all monoclonal antibody reagent combinations used to stain the sample.

15. The process according to claim 14, wherein each combination of monoclonal antibody reagents contains, in addition to the monoclonal antibodies, other probes of comprising fluorochromes specific for the measurement of nucleic acid dyes, mitochondria, and other cell components and cell functions.

16. The process according to claim 13, wherein each combination of multiple monoclonal antibodies has a number of fluorescence emissions comprising two or more different fluorochromes, each linked to a different monoclonal antibody, whose fluorescence emission is distinguishable from that of the other fluorochrome-conjugated monoclonal antibody reagents in the combination.

17. The process according to claim 1, wherein each monoclonal antibody in each combination is conjugated to a different fluorochrome and each combination of monoclonal antibodies has, in common, one or more fluorochrome-conjugated monoclonal antibody reagents.

18. The process according to claim 1, wherein a combination of compatible fluorochromes is selected from fluorescein isothiocyanate (FITC), phycoerythrin (PE), peridin chlorophyll protein (PerCP), allophycocyanin, alexa fluor 488, alexa 647, alexa fluor 610, alexa 710, alexa fluor 405, cyanin 5 (Cy5), Cyanin 5.5 (Cy5.5), pacific blue (PB), cascade yellow, cascade blue and conjugates thereof coupled with PE, to APC or to PerCP (e.g. PE/Cy5, PE/Cy5.5, PE/Cy7, PerCP/Cy5.5, APC/Cy7), quantum dots or any additional compatible fluorochrome or fluorochrome tandem.

19. The process according to claim 1, wherein one data file is stored for each sample aliquot measured in the flow cytometer.

20. The process according to claim 1, wherein one data file is stored which contains data for two or more sample aliquots measured in the flow cytometer.

21. The process according to claim 1, wherein an identical number of events are measured for each sample aliquot.

22. The process according to claim 1, wherein different numbers of events are measured for each sample aliquot.

23. The process according to claim 1, wherein all those parameters common to each pair of sample aliquots are also common to all other sample aliquots measured whose information is contained in the fused data file.

24. The process according to claim 1, wherein only part of all those parameters common to each pair of sample aliquots, are also common to all other sample aliquots measured whose information is contained in the fused data file.

25. The process according to claim 1, wherein the original data files and the events contained in each of said data files are pasted in a sequence directly related to the sequence they were measured in the flow cytometer.

26. The process according to claim 1, wherein the original data files and the events contained in each of said data files are pasted in a sequence inversely related to the sequence they were measured in the flow cytometer.

27. The process according to claim 1, wherein the original datafiles and the events contained in each of said data files are pasted in a sequence which is not related to the sequence that they were measured in the flow cytometer.

28. The process according to claim 1, wherein the sequence of parameters in the columns of the fused data file is directly related to the sequence they were measured in the flow cytometer.

29. The process according to claim 1, wherein the sequence of parameters in the columns of the fused data file is inversely related to the sequence they were measured in the flow cytometer.

30. The process according to claim 1, wherein the sequence of parameters in the columns of the fused data file is not related to the sequence they were measured in the flow cytometer.

31. The process according to claim 1, wherein the overall number of parameters estimated for which values are assigned to each individual cellular event included in the new fused data file is equal to or lower than the total number of parameters which differ between two or more of the sample aliquots measured in the flow cytometer.

32. The process according to claim 1, wherein similarity-based statistical estimation approaches are used to calculate values and a corresponding uncertainty measure for those parameters not measured for a group of events in the fused data file.

33. The process according to claim 1, wherein to calculate values and a corresponding uncertainty measure for those parameters not measured for a group of events in the fused data file, all parameters common to two or more files are used.

34. The process according to claim 1, wherein to calculate values and a corresponding uncertainty measure for those parameters not measured for a group of events in the fused data file, only a part of all parameters common to two or more files are used.

35. The process according to claim 1, wherein to calculate values and a corresponding uncertainty measure for those parameters not measured for a group of events in the fused data file, all events in the fused data file are used.

36. The process according to claim 1, wherein to calculate values and a corresponding uncertainty measure for those parameters not measured for a group of events in the fused data file, only part of all events in the fused data file are used.

37. The process according to claim 1, wherein the calculation of values and a corresponding uncertainty measure for those parameters not measured for a group of events in the fused data file, is performed for single events.

38. The process according to claim 1, wherein the calculation of values and a corresponding uncertainty measure for those parameters not measured for a group of events in the fused data file, is performed for a group of two or more events.

39. The process according to claim 1, wherein one or more of the measured parameters in one or more sample aliquots may also be estimated and used as an internal quality control of the estimation procedure.

40. The process according to claim 1, wherein the new data file containing both the measured data measured in the flow cytometer for each event of the individual original data files and the estimated data for those parameters not measured in a group of events from one or more of the original data files, is analyzed using conventional flow cytometry software programs.

* * * * *

UNITED STATES PATENT AND TRADEMARK OFFICE
CERTIFICATE OF CORRECTION

PATENT NO. : 7,321,843 B2  Page 1 of 1
APPLICATION NO. : 11/240167
DATED : January 22, 2008
INVENTOR(S) : Orfao De Matos Correia It is certified that error appears in the above-identified patent and that said Letters Patent is hereby corrected as shown below:

In particular, in Column 10, line 44 (Line 1 of Claim 4), please change "claim 2" to correctly read: --claim 3--.

Signed and Sealed this

Sixth Day of May, 2008

JON W. DUDAS
*Director of the United States Patent and Trademark Office*